(12) United States Patent
Jeroro et al.

(10) Patent No.: US 11,103,859 B2
(45) Date of Patent: Aug. 31, 2021

(54) UZM-54 AND TRANSALKYLATION PROCESS USING SAME

(71) Applicant: UOP LLC, Des Plaines, IL (US)

(72) Inventors: Eseoghene Jeroro, Schaumburg, IL (US); Deng-Yang Jan, Elk Grove Village, IL (US); Pelin Cox, Des Plaines, IL (US); Jaime G. Moscoso, Mount Prospect, IL (US); Martha Leigh Abrams, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/734,469

(22) Filed: Jan. 6, 2020

(65) Prior Publication Data

US 2021/0205795 A1 Jul. 8, 2021

(51) Int. Cl.
| | | |
|---|---|---|
| *B01J 29/80* | (2006.01) | |
| *B01J 29/18* | (2006.01) | |
| *B01J 29/40* | (2006.01) | |
| *C07C 6/12* | (2006.01) | |
| *C07C 15/08* | (2006.01) | |
| *B01J 35/10* | (2006.01) | |

(52) U.S. Cl.
CPC .............. *B01J 29/80* (2013.01); *B01J 29/18* (2013.01); *B01J 29/40* (2013.01); *C07C 6/126* (2013.01); *B01J 35/1019* (2013.01); *C01P 2002/72* (2013.01); *C07C 15/08* (2013.01); *C07C 2529/18* (2013.01); *C07C 2529/40* (2013.01); *C07C 2529/80* (2013.01)

(58) Field of Classification Search
None
See application file for complete search history.

(56) References Cited

U.S. PATENT DOCUMENTS

| | | |
|---|---|---|
| 7,626,064 B1 | 12/2009 | Boldingh et al. |
| 9,890,094 B2 | 2/2018 | Kuzmanich et al. |
| 10,166,532 B2 | 1/2019 | Kuzmanich et al. |
| 10,167,201 B2 | 1/2019 | Moscoso et al. |
| 2012/0083636 A1* | 4/2012 | Boldingh ............... C07C 6/126 585/401 |
| 2016/0256857 A1 | 9/2016 | Moscoso et al. |
| 2016/0257632 A1 | 9/2016 | Kuzmanich et al. |

(Continued)

FOREIGN PATENT DOCUMENTS

| | | |
|---|---|---|
| IN | 201847025652 A | 7/2018 |
| WO | 2005095309 A1 | 10/2005 |

(Continued)

OTHER PUBLICATIONS

Rouquerol, J. et al., Is the BET Equation Applicable to Microporous Adsorbents?, Studies in Surface Science and Catalysis 160, 2007 Elsevier B.V.

(Continued)

*Primary Examiner* — Philip Y Louie
*Assistant Examiner* — Alyssa L Cepluch

(57) ABSTRACT

A catalyst suitable for the conversion of aromatic hydrocarbons is described. The catalyst comprises UZM-54 zeolite; a mordenite zeolite; a binder comprising alumina, silica, or combinations, thereof; and a metal selected from one or more of: Groups VIB(6) VIIB(7), VIII(8-10) and IVA(14) of the Periodic Table. A process for transalkylation using the catalyst is also described.

12 Claims, 2 Drawing Sheets

(56) References Cited

U.S. PATENT DOCUMENTS

2018/0369795 A1* 12/2018 Mauer ..................... B01J 29/80
2020/0207631 A1* 7/2020 Gallego Sanchez ..... B01J 29/40

FOREIGN PATENT DOCUMENTS

| WO | 2018011122 A1 | 1/2018 | | |
|---|---|---|---|---|
| WO | 2018104471 A1 | 6/2018 | | |
| WO | WO-2018224711 A1 * | 12/2018 | ............. | C01B 39/48 |

OTHER PUBLICATIONS

Written Opinion from PCT application No. PCT/US2021/012133 dated Feb. 17, 2021.
International Search Report from PCT application No. PCT/US2021/012133 dated Mar. 25, 2021.

* cited by examiner

UZM-54 AND TRANSALKYLATION PROCESS USING SAME

BACKGROUND

Xylene isomers are produced in large volumes from petroleum as feedstocks for a variety of important industrial chemicals. The most important of the xylene isomers is para-xylene, the principal feedstock for polyester which continues to enjoy a high growth rate from a large base demand. Ortho-xylene is used to produce phthalic anhydride, which has high-volume but mature markets. Meta-xylene is used in lesser but growing volumes for such products as plasticizers, azo dyes, and wood preservers. Ethylbenzene is typically present in xylene mixtures and is occasionally recovered for styrene production but is usually considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand. Consequently, conversion of other hydrocarbons is necessary to increase the yield of xylenes and benzene. Toluene is commonly dealkylated to produce benzene or disproportionated to yield benzene and $C_8$ aromatics from which the individual xylene isomers are recovered. More recently, processes have been commercialized to transalkylate heavier aromatics along with toluene selectively to increase the yield of xylenes from aromatics complexes.

The art teaches a variety of catalysts for the transalkylation of aromatic hydrocarbons. A wide range of zeolites, including mordenite, have been disclosed as effective transalkylation catalysts. Shaped catalysts, multiple zeolites, metal modifiers, and treatments such as steam calcination have been described as pathways for increasing the effectiveness of the catalysts. There is a need to improve xylene productivity with lower aromatic ring destruction and improved stability with an increased conversion of heavy material.

DESCRIPTION OF THE INVENTION

Figure 1:
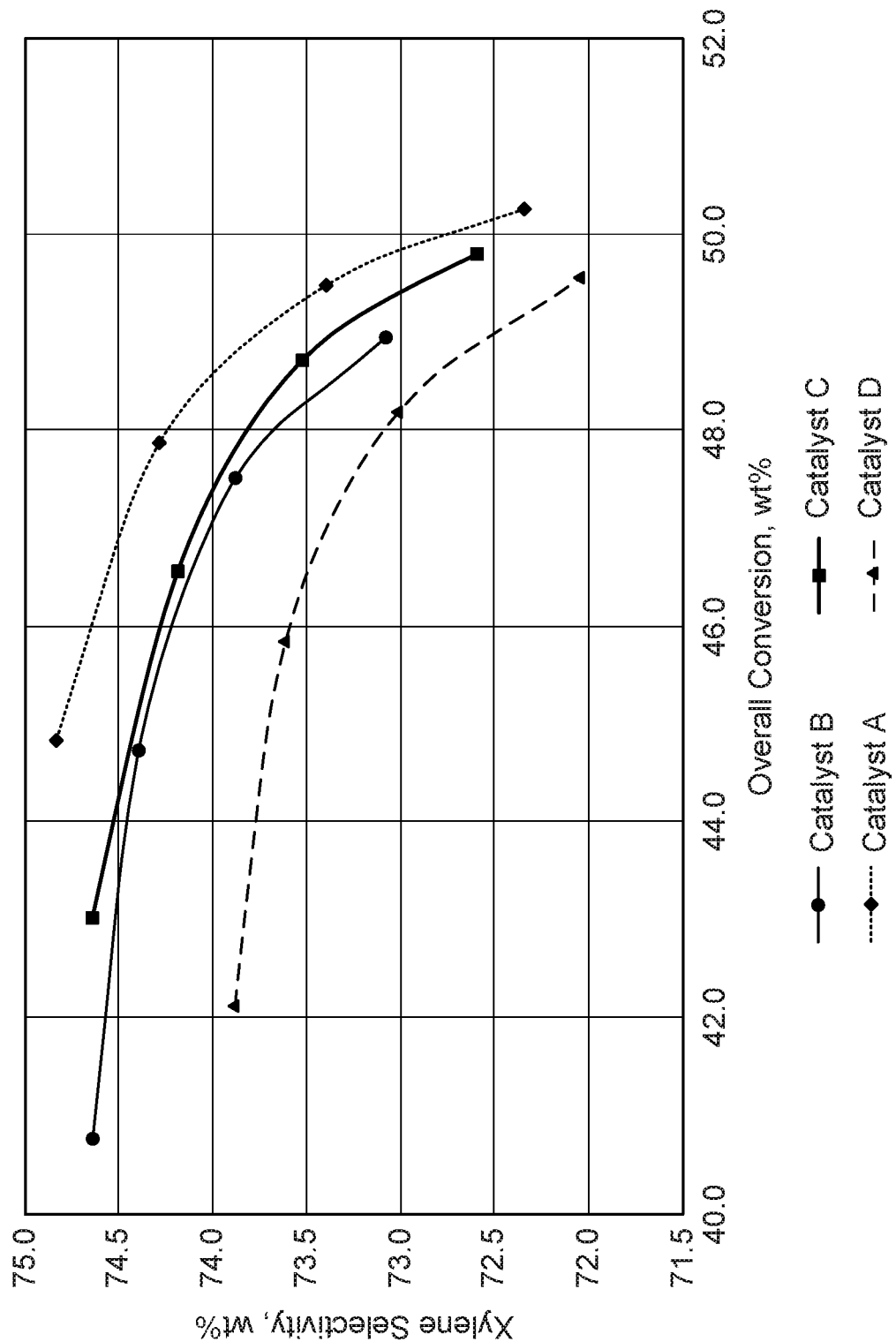
FIG. 1 is graph comparing the xylene selectivity of a transalkylation catalyst made with the UZM-54 zeolite with catalysts made with several commercial MFI zeolites.

This invention is unique because the catalyst comprises a UZM-54 zeolite, a mordenite zeolite, a binder, and a metal. UZM-54 combines the characteristics of improved mass transport (small crystal) and high acid density (low $Si/Al_2$ ratio) to increase the efficiency (selectivity and activity) to xylene in a process involving enhanced dealkylation reactivity of $C_{2+}$ alkyl groups from aromatic feedstocks and transalkylation of toluene and heavy aromatics. As a result of enhanced reaction pathways leading to xylene production, retention of phenyl rings is further increased.

The catalyst has improved performance in transalkylation, in particular, an increase in the xylene selectivity of 0.1-1.1 wt-% versus other medium pore zeolites (MFI framework), and an increase in phenyl retention or a decrease in aromatic ring loss of 0.2 mol % as measured by a standard pilot plant test with 50/50 toluene/$A_{9+}$ feed.

The UZM-54 zeolite is a small crystal nanopentasil zeolite with a low $Si/Al_2$ ratio of about 22 to about 60, and crystallite size of less than about 30 nm as measured by XRD Rietveld refinement, and a mesopore surface area greater than about 80 and less than about 300 m²/g. Details of this material and methods of preparation can be found in U.S. Pat. Nos. 9,890,094, 10,010,878, 10,166,532, and 10,167,201, each of which is incorporated herein in its entirety.

Any mordenite zeolite can be used. Suitable commercially available mordenite zeolites include, but are not limited to, UZM-14 from UOP, CZM 20 from Clariant, or 640HOA from Tosoh.

The binder can be alumina, silica, or combinations thereof. In some embodiments, the binder is alumina. The binder comprises one or more of alumina, silica and silica-alumina. Alumina is an especially preferred refractory inorganic oxide for use herein, particularly with respect to the manufacture of a catalytic composite for use in the transalkylation of alkylaromatic hydrocarbons. The alumina can be those of transitional phases comprising gamma-, theta-, delta-, eta-alumina or high temperature phase such as alpha-alumina, Preferably, alumina is gamma-alumina. The alumina may be incorporated into the catalyst using any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred.

The metal can be one or more metals from Groups VIB(6) VIIB(7), VIII(8-10) and IVA(14) of the Periodic Table. In some embodiments, the metals are Mo, Ni, Re, Pt, or Pd, or combinations thereof.

In one embodiment, the binder is alumina, and the metal is one or more of Mo, Ni, Re, Pt, or Pd.

The catalyst typically comprises about 20 to about 60 wt % of the UZM-54, about 20 to about 60 wt % of the mordenite zeolite, about 10 to about 40 wt % of the binder, and about 0.1 to about 10 wt % of the metal. In some embodiments, the catalyst comprises about 20 to about 30 wt % of the UZM-54, about 45 to about 55 wt % of the mordenite zeolite, about 20 to about 30 wt % of the binder, and about 1 to about 5 wt % of the metal.

The catalyst may contain about 20 to about 60 wt % of the UZM-54, or about 20 to about 50 wt %, or about 20 to about 40 wt %, or about 20 to about 30 wt %, or about 22 to about 28 wt %, or about 25 to about 60 wt %, or about 30 to about 60 wt %, or about 40 to about 60 wt %, or about 45 to about 55 wt %. The catalyst may contain about 20 to about 60 wt % of the mordenite zeolite, or about 20 to about 50 wt %, or about 20 to about 40 wt %, or about 20 to about 30 wt %, or about 22 to about 28 wt %, or about 25 to about 60 wt %, or about 30 to about 60 wt %, or about 40 to about 60 wt % or about 45 to about 55 wt %. The catalyst may contain about 10 to about 40 wt % of the binder, or about 10 to about 35 wt %, or about 10 to about 30 wt %, or about 15 to about 40 wt %, or about 20 to about 40 wt %, or about 25 to about 40 wt %, or about 30 to about 40 wt %. The catalyst may contain about 0.1 to about 10 wt % of the metal, or about 0.1 to about 7 wt %, or about 0.1 to about 5 wt %, or about 0.5 to about 10 wt %, or about 0.5 to about 7 wt %, or about 0.5 to about 5 wt %, or about 1 to about 10 wt %, or about 1 to about 7 wt %, or about 1 to about 5 wt %.

The UZM-54 zeolite can optionally be ion exchanged by contacting it with an ammonium salt, including but not limited to, ammonium nitrate, ammonium chloride, ammonium sulfate, and the like at a temperature of 70 to 80° C. for 2 to 6 hours.

The UZM-54 zeolite (optionally ion exchanged) can be used in a catalyst preparation. It can be combined with the mordenite zeolite, binders, and metals as described below.

The UZM-54 zeolite, the mordenite zeolite, and the binder may be combined in any conventional or otherwise convenient manner to form spheres, pills, pellets, granules, extrudates, or other suitable particle shape. For example, finely divided zeolite and metal salt particles can be dispersed in an alumina sol, and the mixture in turn dispersed as droplets in a hot oil bath whereby gelation occurs with the formation of spheroidal gel particles. The method is described in greater detail in U.S. Pat. No. 2,620,314. A preferred method comprises comingling a finely divided form of the selected zeolite, refractory inorganic oxide and a metal salt with a binder and/or lubricant and compressing the mixture into pills or pellets of uniform size and shape. Alternatively, and still more preferably, the zeolite, refractory inorganic oxide and metal salt are combined and admixed with a peptizing agent in a mix-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobates, with a trilobe form being favored. The extrudates also may be formed into spheres by means of a spinning disc or drum and then dried and calcined.

The metal can be introduced by either co-mulling during the extrusion or impregnation.

The catalyst may be subjected to a presulfiding step to incorporate from about 0.05 to about 3 wt.-% sulfur on an elemental basis, or about 0.05 to about 2 wt.-%. This presulfiding step may take place either during the manufacture of the catalyst or after the catalyst has been loaded into a process unit.

The finished composite is preferably calcined in an air atmosphere at a temperature of from about 425° C. to about 750° C., preferably at a temperature of from about 475° C. to about 575° C., over a period of from about 0.5 to about 10 hours.

The feedstream to the present process comprises alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyl-dimethylbenzenes, diethylbenzenes, methylpropylbenzenes, ethylpropylbenzenes, triethylbenzenes, diisopropylbenzenes, and mixtures thereof.

The aromatics-rich feed stream to a transalkylation or disproportionation process may be derived from a variety of sources, including without limitation catalytic reforming, pyrolysis of naphtha, distillates or other hydrocarbons to yield light olefins and heavier aromatics-rich byproducts, and catalytic or thermal cracking of heavy oils to yield a stream rich in single-ring aromatics. Products from pyrolysis or other cracking operations generally will be hydrotreated according to processes well known in the industry before being charged to the complex in order to remove sulfur, nitrogen, olefins and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of non-aromatics in the product. The reformate also advantageously is subjected to olefin saturation to remove potential process contaminants and materials that could polymerize to heavy non-convertibles in a transalkylation process. Such processing steps are described in U.S. Pat. No. 6,740,788 B1, incorporated herein by reference thereto.

The feed stream to a transalkylation or disproportionation process can be a substantially pure alkylaromatic hydrocarbon of from about 6 to about 15 carbon atoms, a mixture of such alkylaromatic hydrocarbons, or a hydrocarbon fraction rich in said alkylaromatics. The feed stream comprises alkylaromatic hydrocarbons of the general formula $C_6H_{(6-n)}R_n$, where n is an integer from 1 to 5 and R is one or more of $CH_3$, $C_2H_5$, $C_3H_7$, $C_4H_9$, or $C_5H_{11}$ in any combination. The feed stream also may comprise benzene and aromatics having from 2 to 4 rings. Suitable components of the feed stream thus generally include, for example but without so limiting the invention, benzene, toluene, ethylbenzene, meta-xylene, ortho-xylene, para-xylene, ethyl-toluenes, trimethylbenzenes, diethyl-benzenes, triethylbenzenes, propylbenzenes, butylbenzenes, methylpropylbenzenes, ethylpropylbenzenes, diisopropylbenzenes, butylbenzenes, indanes, naphthalenes, tetralins, decalins, biphenyls, diphenyls and fluorenes. The feed stream also may contain lesser concentrations of nonaromatics such as pentanes, hexanes, heptanes and heavier paraffins, along with methylcyclopentane, cyclohexane and heavier naphthenes; pentanes and lighter paraffins generally will have been removed before processing in the aromatics complex. The combined transalkylation feed preferably contains no more than about 10 wt-% nonaromatics; olefins preferably are restricted to a Bromine Index of no more than about 1500, and preferably no more than about 500.

A preferred component of the feedstock is a heavy-aromatics stream comprising $C_9$ aromatics, thereby effecting transalkylation of toluene and $C_9$ aromatics to yield additional xylenes. Benzene may also be transalkylated to yield additional toluene. Indane may be present in the heavy-aromatics stream, although it is not a desirable component to effect high yields of $C_8$ aromatics product. $C_{10+}$ aromatics also may be present, preferably in an amount of 30% or less of the feed. The heavy-aromatics stream preferably comprises at least about 90 mass-% aromatics, and may be derived from the same or different known refinery and petrochemical processes as the benzene and toluene feedstock and/or may be recycled from the separation of the product from transalkylation.

The feedstock is typically transalkylated in the vapor phase and in the presence of hydrogen. If transalkylated in the liquid phase, then the presence of hydrogen is optional. If present, free hydrogen is associated with the feedstock and recycled hydrocarbons in an amount of from about 0.1 moles per mole of alkylaromatics up to 10 moles per mole of alkylaromatics. This ratio of hydrogen to alkylaromatics is also referred to as hydrogen to hydrocarbon ratio. The transalkylation reaction preferably yields a product having an increased xylene content and also comprises benzene.

The feed to a transalkylation reaction zone usually first is heated by indirect heat exchange against the effluent of the reaction zone and then is heated to reaction temperature by exchange with a warmer stream, steam or a furnace. The feed then is passed through a reaction zone, which may comprise one or more individual reactors. Passage of the combined feed through the reaction zone effects the production of an effluent stream comprising unconverted feed and product hydrocarbons. This effluent is normally cooled by indirect heat exchange against the stream entering the reaction zone and then further cooled through the use of air or cooling water. The effluent may be passed into a stripping column in which substantially all $C_5$ and lighter hydrocarbons present in the effluent are concentrated into an overhead stream and removed from the process. An aromatics-rich stream is recovered as net stripper bottoms which is referred to herein as the transalkylation effluent.

The transalkylation or disproportionation reaction can be effected in contact with the catalytic composite of this invention in any conventional or otherwise convenient manner and may comprise a batch or continuous type of operation, with a continuous operation being preferred. The catalyst usefully is disposed as a fixed bed in a reaction zone of a vertical tubular reactor with the alkylaromatic feed stock charged through the bed in an upflow or downflow manner.

Conditions employed in the transalkylation zone normally include a temperature of from about 200° C. to about 540° C., preferably between about 200° C. to about 480° C. The transalkylation zone is operated at moderately elevated pressures broadly ranging from about 100 kPa to about 6 MPa absolute. The transalkylation reaction can be effected over a wide range of space velocities, i.e., weight of charge per weight of catalyst per hour, weight hourly space velocity generally is in the range of from about 0.1 to about 20 $hr^{-1}$.

The transalkylation effluent is separated into a light recycle stream, a mixed $C_8$ aromatics product and a heavy-aromatics stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all the $C_9$ and heavier aromatics and may be partially or totally recycled to the transalkylation reaction zone.

EXAMPLES

Example 1—Preparation of the Transalkylation Catalyst Containing the UZM-54 and Commercial Zeolite The properties of the UZM-54 and other commercial zeolites are given in Table 1. The BET surface area results are calculated with the modified Rouquerol method using uptake data collected at P/PO of about 0.01 to 0.04, and t-plot using a thickness of 3.5-5.0 A. The BET external surface area is the difference between the BET total surface area and the BET micropore surface area. The silica-to-alumina ratio is determined by ICP analysis and the crystallite size results by XRD Rietveld refinement. The Rietveld refinements were performed using an orthorhombic MFI structure model and the Bruker TOPASv6 software. Instrument-related broadening was accounted for using the fundamental parameters approach. Values reported are the LVol-FWHM results, which means the volume-weighted column heights (LVol) calculated from the Voight-FWHM. The shape factor used was 0.89 i.e. assuming a spherical crystallite. Compared to the other commercial zeolites, UZM-54 has a smaller crystallite size by XRD Rietveld refinement, and a higher BET external surface area. These properties improve the mass transport within its framework and result in a higher xylenes selectivity, higher phenyl retention, and lower by-product formation in the transalkylation reaction.

TABLE 1

Properties of UZM-54 and commercial MFI zeolites

| Finished catalyst | A | B | C | D |
|---|---|---|---|---|
| Zeolite | UZM-54 | GNZ | DNZ | CBV-2314 |
| Silica/alumina ratio | 26 | 55 | 30 | 23 |
| BET total surface area, m2/g | 435 | 354 | 316 | 334 |
| BET micropore surface area, $m^2/g$ | 269 | 304 | 279 | 294 |
| BET external surface area, $m^2/g$ | 166 | 50 | 37 | 40 |
| Crystallite size, nm | 17-30 | >70 | >70 | >80 |

Example 2—Preparation of the Transalkylation Catalyst Containing the UZM-54 and Commercial Zeolite The UZM-54 zeolite is first ion-exchanged. The ion-exchange steps are given below.

2573.8 g of water and 217.2 g of ammonium nitrate powder were added to a stainless-steel beaker. 200 g of the UZM-54 zeolite was added to the beaker. The stir plate was heated to 75° C. and the slurry was held at 75° C. for 1 hour. The beaker was removed from the stir plate, and the slurry was filtered over a Buchner funnel using filter paper type 52. Once the nitrate solution has been filtered through, the ion exchanged material was rinsed with 2500 ml of water to remove any excess nitrates. The ion exchange was repeated two more times. The sample was re-slurried for each ion exchange. After the water washing was complete, the sample was dried at 100° C. overnight.

A powder blend made up of the ion-exchanged UZM-54 or a commercial MFI zeolite in its ammonium or proton form, the mordenite zeolite in its ammonium or proton form, and the binder was placed in a muller and dry mulled for about 15 minutes. A nitric acid solution of about 18-20 wt % was subsequently added to the powder blend and mulled for about 15 minutes. An ammonium heptamolybdate (AHM) solution was added and the mixture containing the powder blend, nitric acid solution, and AHM solution was mulled for about 15 minutes. An additional amount of water was added to the aforementioned mixture to obtain an LOI (Loss of Ignition) of between 35 to 50 wt % to attain an extrudable dough consistency.

The dough was extruded through a die plate containing die holes with a diameter in the range of 1/32 to 1/8 inches, and the green extrudate was collected and dried at 100° C. for 2 to 12 hours.

The dried extrudate base was sized to 10×12 mesh and then calcined at a temperature between 500 and 580° C. for 4 hours in a box oven.

Example 3—Test Results of Transalkylation Catalysts with a Toluene and Heavy Aromatics Feed Four catalysts (A, B, C, D) were prepared with the same composition following the procedure described in Example 2. Catalyst A was made with the UZM-54 zeolite while catalysts B, C, and D were made with commercial MFI zeolites, GNZ from Hejia Chemical, DNZ from Hejia Chemical and CBV-2314 from Zeolyst. The catalysts were extruded as a 1/16-inch cylinder, and the composition was 29.6 wt % UZM-54 or MFI, 29.6 wt % UZM-14, 39.4 wt % alumina, and 1.50 wt % $MoO_3$. The catalysts were tested in a transalkylation reaction using a feed of 50 wt % toluene and 50 wt % A9+ aromatics. The A9+ aromatics feed was nominally 50 wt % trimethylbenzene, with the remaining 50 wt % composed of a mixture of A9+ components, such as methylethylbenzene and dimethylethylbenzene. The transalkylation reaction conditions were a WHSV of 3.5 $hr^{-1}$, a molar ratio of hydrogen to feed of 3, a pressure of 2.8 MPa(g) (400 psig), and temperatures from 310° C. to 360° C. to generate a range of different conversions.

Figure 2:
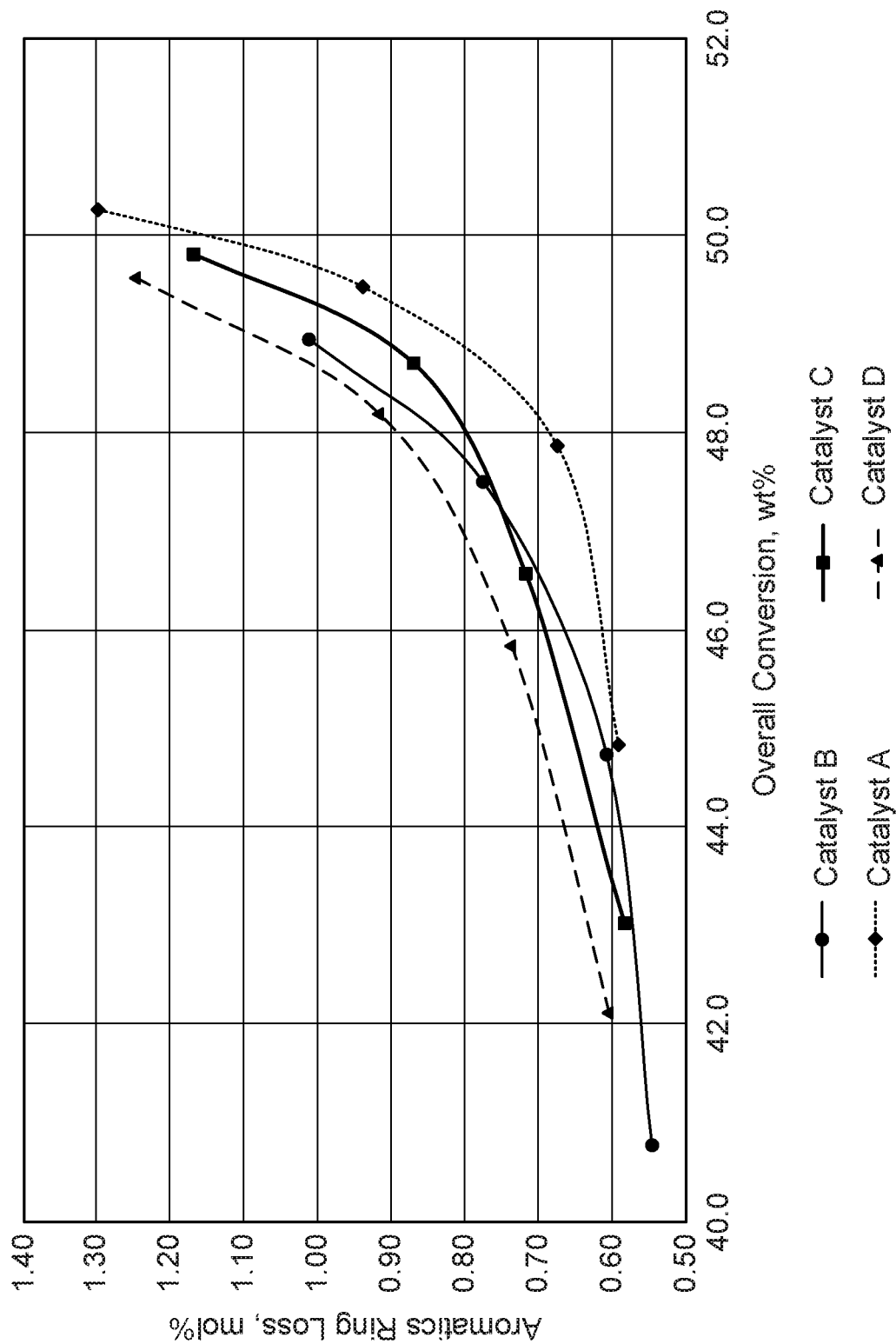
FIG. 2 is graph comparing the aromatic ring loss of a transalkylation catalyst made with the UZM-54 zeolite with catalysts made with several commercial MFI zeolites.

FIGS. 1 and 2 show the results of the transalkylation reactions. Compared to the catalyst containing the UZM-54 zeolite, the catalysts made up of commercial MFI zeolite samples show a lower xylene selectivity and higher aromatic ring loss at any given conversion. Note that aromatic ring loss in mol % is defined by [(moles of aromatic rings in feed-moles of aromatic rings in product/moles of aromatic rings in feed*100%]. It represents the amount of aromatic rings lost in the unconverted feed that is recirculated in the process. The higher xylene selectivity and lower aromatic ring loss observed for the catalyst made from the UZM-54 zeolite shows that compared to the commercial MFI zeolite samples, UZM-54 is more efficient at converting the aromatic compounds in the transalkylation feed to the desired xylene product, with fewer losses of the aromatic ring to undesired by products.

By the term "about," we mean within plus or minus 10% of the value, or plus or minus 5%, or plus or minus 1%.

SPECIFIC EMBODIMENTS

While the following is described in conjunction with specific embodiments, it will be understood that this description is intended to illustrate and not limit the scope of the preceding description and the appended claims.

A first embodiment of the invention is a composition suitable for the conversion of aromatic hydrocarbons comprising UZM-54 zeolite; a mordenite zeolite; a binder comprising alumina, silica, or combinations, thereof; and a metal selected from one or more of Groups VIB(6) VIIB(7), VIII(8-10) and IVA(14) of the Periodic Table. An embodiment of the invention is one, any or all of prior embodiments in this paragraph up through the first embodiment in this paragraph wherein the catalyst comprises about 20 to about 60 wt % of the UZM-54 zeolite, about 20 to about 60 wt % of the mordenite zeolite, about 10 to about 40 wt % of the binder, and about 0.1 to about 10 wt % of the metal. An embodiment of the invention is one, any or all of prior embodiments in this paragraph up through the first embodiment in this paragraph wherein the UZM-54 zeolite has less than about 500 wppm Na. An embodiment of the invention is one, any or all of prior embodiments in this paragraph up through the first embodiment in this paragraph wherein the binder comprises alumina. An embodiment of the invention is one, any or all of prior embodiments in this paragraph up through the first embodiment in this paragraph wherein the metal comprises one or more of Mo, Ni, Re, Pt, or Pd. An embodiment of the invention is one, any or all of prior embodiments in this paragraph up through the first embodiment in this paragraph wherein the catalyst comprises about 20 to about 60 wt % of the UZM-54 zeolite; about 20 to about 60 wt % of the mordenite zeolite; about 10 to about 40 wt % of the binder; and, about 0.1 to about 10 wt % of the metal wherein the metal comprises one or more of Mo, Ni, Re, Pt, or Pd. An embodiment of the invention is one, any or all of prior embodiments in this paragraph up through the first embodiment in this paragraph wherein the UZM-54 zeolite has less than about 500 wppm Na. An embodiment of the invention is one, any or all of prior embodiments in this paragraph up through the first embodiment in this paragraph wherein the binder comprises alumina.

A second embodiment of the invention is a process for transalkylation of a feedstream comprising one or more of $C_7$, $C_9$, $C_{10}$ and $C_{11+}$ aromatics to obtain a product stream having an increased concentration of $C_8$ aromatics relative to that of the feedstream, comprising contacting the feedstream at transalkylation conditions with a catalyst comprising UZM-54 zeolite; a mordenite zeolite; a binder comprising alumina, silica, or combinations, thereof; and a metal selected from one or more of Groups VIB(6) VIIB(7), VIII(8-10) and IVA(14) of the Periodic Table. An embodiment of the invention is one, any or all of prior embodiments in this paragraph up through the second embodiment in this paragraph wherein the feedstream further comprises benzene. An embodiment of the invention is one, any or all of prior embodiments in this paragraph up through the second embodiment in this paragraph wherein the feedstream further comprises $C_8$ aromatics. An embodiment of the invention is one, any or all of prior embodiments in this paragraph up through the second embodiment in this paragraph wherein the feedstream further comprises aromatic compounds having from 2 to 4 rings. An embodiment of the invention is one, any or all of prior embodiments in this paragraph up through the second embodiment in this paragraph wherein the feedstream further comprises a bottoms stream from the fractionation of $C_8$ aromatics from the transalkylation product stream. An embodiment of the invention is one, any or all of prior embodiments in this paragraph up through the second embodiment in this paragraph wherein the transalkylation conditions comprise one or more of a temperature from about 200° C. to about 540° C., a pressure from about 100 kPa to about 6 MPa absolute, or a space velocity from about 0.1 to about 20 $hr^{-1}$. An embodiment of the invention is one, any or all of prior embodiments in this paragraph up through the second embodiment in this paragraph wherein the catalyst comprises about 20 to about 60 wt % of the UZM-54 zeolite, about 20 to about 60 wt % of the mordenite zeolite, about 10 to about 40 wt % of the binder, and about 0.1 to about 10 wt % of the metal. An embodiment of the invention is one, any or all of prior embodiments in this paragraph up through the second embodiment in this paragraph wherein the UZM-54 zeolite has less than about 500 wppm Na. An embodiment of the invention is one, any or all of prior embodiments in this paragraph up through the second embodiment in this paragraph wherein the binder comprises alumina. An embodiment of the invention is one, any or all of prior embodiments in this paragraph up through the second embodiment in this paragraph wherein the metal comprises the metal comprises one or more of Mo, Ni, Re, Pt, or Pd. An embodiment of the invention is one, any or all of prior embodiments in this paragraph up through the second embodiment in this paragraph wherein the catalyst comprises about 20 to about 60 wt % of the UZM-54 zeolite; about 20 to about 60 wt % of the mordenite zeolite; about 10 to about 40 wt % of the binder; and, about 0.1 to about 10 wt % of the metal wherein the metal comprises one or more of Mo, Ni, Re, Pt, or Pd. An embodiment of the invention is one, any or all of prior embodiments in this paragraph up through the second embodiment in this paragraph wherein the binder comprises alumina.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for transalkylation of a feedstream comprising one or more of $C_7$, $C_9$, $C_{10}$ and $C_{11+}$ aromatics to obtain a transalkylation product stream having an increased concentration of $C_8$ aromatics relative to that of the feedstream, comprising contacting the feedstream at transalkylation conditions with a catalyst comprising:
   UZM-54 zeolite;
   a mordenite zeolite;
   a binder comprising alumina, silica, or combinations, thereof; and
   a metal selected from one or more of: Groups VIB(6) VIIB(7), VIII(8-10) and IVA(14) of the Periodic Table.

2. The process of claim 1 wherein the feedstream further comprises benzene.

3. The process of claim 1 wherein the feedstream further comprises $C_8$ aromatics.

4. The process of claim 1 wherein the feedstream further comprises aromatic compounds having from 2 to 4 rings.

5. The process of claim 1 wherein the feedstream further comprises a bottoms stream from fractionation of $C_8$ aromatics from the transalkylation product stream.

6. The process of claim 1 wherein the transalkylation conditions comprise one or more of: a temperature from about 200° C. to about 540° C., a pressure from about 100 kPa to about 6 MPa absolute, or a weight hourly space velocity from about 0.1 to about 20 $hr^{-1}$.

7. The process of claim 1 wherein the catalyst comprises about 20 to about 60 wt % of the UZM-54 zeolite, about 20 to about 60 wt % of the mordenite zeolite, about 10 to about 40 wt % of the binder, and about 0.1 to about 10 wt % of the metal.

8. The process of claim 1 wherein the UZM-54 zeolite has less than about 500 wppm Na.

9. The process of claim 1 wherein the binder comprises alumina.

10. The process of claim 1 wherein the metal comprises one or more of: Mo, Ni, Re, Pt, or Pd.

11. The process of claim 1 wherein the catalyst comprises
   about 20 to about 60 wt % of the UZM-54 zeolite;
   about 20 to about 60 wt % of the mordenite zeolite;
   about 10 to about 40 wt % of the binder; and,
   about 0.1 to about 10 wt % of the metal wherein the metal comprises one or more of: Mo, Ni, Re, Pt, or Pd.

12. The process of claim 11 wherein the binder comprises alumina.

* * * * *